United States Patent
Kim

(10) Patent No.: US 9,999,365 B2
(45) Date of Patent: Jun. 19, 2018

(54) MAPPING ABLATION CATHETER

(71) Applicant: Korea University Research and Business Foundation, Seoul (KR)

(72) Inventor: Young Hoon Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 160 days.

(21) Appl. No.: 14/766,958

(22) PCT Filed: Aug. 21, 2014

(86) PCT No.: PCT/KR2014/007765
§ 371 (c)(1),
(2) Date: Aug. 10, 2015

(87) PCT Pub. No.: WO2015/026174
PCT Pub. Date: Feb. 26, 2015

(65) Prior Publication Data
US 2016/0008060 A1    Jan. 14, 2016
US 2016/0361113 A9    Dec. 15, 2016

(30) Foreign Application Priority Data

Aug. 23, 2013 (KR) .......... 10-2013-0100042
Aug. 23, 2013 (KR) .......... 10-2013-0100043

(51) Int. Cl.
*A61B 5/042*     (2006.01)
*A61B 18/14*    (2006.01)
(Continued)

(52) U.S. Cl.
CPC .............. *A61B 5/0422* (2013.01); *A61B 5/04* (2013.01); *A61B 18/1492* (2013.01);
(Continued)

(58) Field of Classification Search
CPC .................... A61B 5/0422; A61B 18/1492
See application file for complete search history.

(56) References Cited

U.S. PATENT DOCUMENTS 5,843,075 A * 12/1998 Taylor ............... A61B 5/0422
600/374
8,475,450 B2    7/2013 Govari et al.
(Continued)

FOREIGN PATENT DOCUMENTS

CN         1700880 A    11/2005
CN       101484083 A     7/2009
(Continued)

*Primary Examiner* — Lee S Cohen
(74) *Attorney, Agent, or Firm* — NSIP Law

(57) ABSTRACT

A mapping ablation catheter is provided comprising: a catheter conduit having a hollow inner space in which a guide member is disposed; a monitoring electrode unit arranged to surround the outer circumferential surface of the distal portion of the catheter conduit and perform a mapping on the lesion region by being in side-contact with a cardiac organ; an ablation electrode unit arranged to be spaced apart from the monitoring electrode unit and surround the outer circumferential surface of the distal portion of the catheter conduit and which removes the lesion region; a plurality of liquid discharge holes arranged on the outer circumferential surface of the ablation electrode; a current application unit which applies current to the monitoring electrode unit and the ablation electrode unit; and a liquid supply unit having a liquid supply tube, one end of the liquid-supply tube connected to the liquid discharge holes in the catheter conduit.

4 Claims, 8 Drawing Sheets

(51) Int. Cl.
*A61B 5/04* (2006.01)
*A61M 25/01* (2006.01)
*A61B 17/00* (2006.01)
*A61B 18/00* (2006.01)

(52) U.S. Cl.
CPC ... *A61M 25/01* (2013.01); *A61B 2017/00053* (2013.01); *A61B 2018/00029* (2013.01); *A61B 2018/00083* (2013.01); *A61B 2018/00351* (2013.01); *A61B 2018/00577* (2013.01); *A61B 2018/00839* (2013.01); *A61B 2018/1472* (2013.01); *A61B 2218/002* (2013.01)

(56) References Cited

U.S. PATENT DOCUMENTS

| | | | |
|---|---|---|---|
| 8,538,501 B2 * | 9/2013 | Venkatachalam | A61B 5/042 600/374 |
| 9,078,667 B2 * | 7/2015 | Besser | A61M 25/0041 |
| 2010/0057074 A1 * | 3/2010 | Roman | A61B 18/1492 606/33 |
| 2013/0006238 A1 * | 1/2013 | Ditter | A61B 18/1492 606/41 |

FOREIGN PATENT DOCUMENTS

| | | |
|---|---|---|
| CN | 101766502 A | 7/2010 |
| JP | 4790236 B2 | 10/2011 |
| JP | 4850697 B2 | 1/2012 |
| KR | 10-2004-0016379 A | 2/2004 |
| KR | 10-2007-0027494 A | 3/2007 |
| KR | 10-2007-0035155 A | 3/2007 |
| KR | 10-0898413 B1 | 5/2009 |
| KR | 10-2010-0021401 A | 2/2010 |
| KR | 10-0949436 B1 | 3/2010 |
| KR | 10-2011-0040898 A | 4/2011 |
| WO | WO 03/030713 A2 | 4/2003 |
| WO | WO 2008/005668 A2 | 1/2008 |
| WO | WO 2010/039443 A1 | 4/2010 |

* cited by examiner

MAPPING ABLATION CATHETER

CROSS REFERENCE TO RELATED APPLICATIONS(S)

This application is a U.S. national phase application under 35 U.S.C. § 371 of PCT Application No. PCT/KR2014/007765 filed on Aug. 21, 2014, which claims the benefit of Korean Patent Application No. 10-2013-0100042, and Korean Patent Application No. 10-2013-0100043 filed on Aug. 23, 2013, the entire disclosures of which are incorporated herein by reference for all purposes.

TECHNICAL FIELD

The present invention relates to a mapping ablation catheter, in particular to a mapping ablation catheter which performs a catheter operation stably by increasing a contact area between lesion region and ablation electrode for removing lesion region.

BACKGROUND ART

Heart beat is performed when a muscle of cardiac organ is stimulated in consecutive order by an electric signal generated periodically from a portion of cardiac organ. However, if there is something wrong with the electric signal flow, a correct heart beat cannot be carried out. This is so-called cardiac arrhythmia.

Fibrillation of heart is the most common continuous arrhythmia and may increase heart rate up to 100 to 175 per minute or more. Fibrillation of heart may cause the frequency of symptom (e.g., atrial flutter, not normal contraction) to be high and may be linked to various aftereffects such as stroke, blood pooling, blood clot, etc.

Treatment of cardiac arrhythmia was quite changed after the introduction of a catheter ablation using high-frequency current. In the catheter ablation technique, under the X-ray control, an ablation-catheter is inserted into the cardiac organ and the tissue causing arrhythmia is destroyed by high-frequency current. Prerequisite for the success of catheter ablation is to detect the cause of arrhythmia in an atrium accurately. The detection is carried out through an electrophysiological test in which recording is performed in a spatial resolution state, using a mapping-catheter in which electrical potentials are inserted into the atrium.

Various minimum invasion electrophysiological procedures use a catheter which arranges at least one electrode near the target tissue region in the cardiac organ. Such a catheter has a relatively long and flexible axis and has an ablation electrode on the end of the catheter. The proximal end of the catheter is connected to a hand portion which may comprise or may not comprise a steering controller for operating the end portion of the catheter.

However, in a conventional catheter as described in KR laid-open publication No. 10-2007-0027494, an ablation electrode to which high current is applied is disposed on the end of the distal portion of the catheter and a mapping electrode which performs a mapping on a lesion is disposed above the electrode to which high current is applied. In case of removing the lesion which is located deep in the cardiac organ, the ablation electrode is in point-contact with the lesion to remove the lesion. However, due to the heart beat, it is difficult to adjust the position of the catheter stably so as to make the ablation electrode contact with the lesion precisely. Here, the term "point contact" means a portion where the end of the ablation electrode is in contact with the lesion.

That is, a portion of the ablation electrode to which high current is applied must be in contact with the lesion in order to remove the lesion. In a configuration that the ablation electrode is arranged on the end of the distal portion, the end of the ablation electrode is in contact with the lesion in the form of cusp. In the description, for clarity's sake, the portion where the end of the ablation electrode is in contact with the lesion will be referred to as "point-contact".

Meanwhile, in case that a plurality of monitoring electrodes for detecting lesion region are attached on the distal end, as can be seen in KR Patent 10-0949436, a catheter is not provided with ablation electrodes and therefore it is difficult of a catheter having a plurality of monitoring electrodes to perform both a mapping and an ablation.

DISCLOSURE OF THE INVENTION

Technical Problem

The object of the present invention is to resolve the above problems and to provide a mapping ablation catheter which have an arrangement to increase the contact area between the ablation electrode and the lesion such that an operator can make the ablation electrode to which high-frequency current is applied be in line-contact or side-contact with the lesion precisely and by which the operator can perform an operation on a person who is under operation stably.

Further, the object of the present invention is to provide a mapping ablation catheter which increases the success rate of the catheter operation. For this, in a direction that the distal portion of the catheter is inserted into the human body, a monitoring electrode is disposed on the end of the catheter and an ablation electrode is disposed above the monitoring electrode. In conventional catheter operation, an ablation electrode is moved to the lesion region by pulling the catheter toward the operator from the lesion region detected by the monitoring electrode. But, in the present invention, the catheter conduit is moved forward from a lesion region detected by the monitoring electrode, by the manipulation of the operator in a direction that the catheter conduit is inserted into the human body. Therefore, the manipulation of the catheter became easier.

Another object of the present invention is to provide a mapping ablation catheter which can detect lesion regions on the cardiac organ with a minimum mapping using a plurality of mapping electrodes, and which can remove lesion regions simultaneously by the plurality of ablation electrodes.

Yet another object of the present invention is to make proximal portions of multiple electrodes of the catheter perform a mapping, to locate the catheter stably, and to perform a stable ablation by the electrodes disposed on the distal portion.

Technical Solution

Preferably, a mapping ablation catheter according to the first embodiment has a distal portion which is inserted into a human body to cure a lesion region, and the catheter comprises: a catheter conduit having a hollow inner space in which a guide member is disposed; a monitoring electrode unit which is arranged to surround the outer circumferential surface of the distal portion of the catheter conduit and which performs a mapping on the lesion region by being in side-contact with a cardiac organ when the catheter conduit is inserted into the cardiac organ; an ablation electrode unit which is arranged to be spaced apart from the monitoring electrode unit and to surround the outer circumferential surface of the distal portion of the catheter conduit and which removes the lesion region when current is applied; a plurality of liquid discharge holes which are arranged on the outer circumferential surface of the ablation electrode; a current application unit which applies current to the monitoring electrode unit and the ablation electrode unit; and a liquid supply unit which has a liquid supply tube, one end of the liquid-supply tube being connected to the liquid discharge holes in the catheter conduit.

In the first embodiment, it is preferable that the mapping a ablation catheter further comprises a hand manipulation unit which is connected to the guide member on the proximal portion of the catheter conduit and which adjusts the curvature of the distal portion of the catheter conduit.

In the first embodiment, it is preferable that the monitoring electrode unit comprises: the first monitoring electrode arranged on the end of the distal portion of the catheter conduit; the second monitoring electrode which is arranged to be spaced apart from the first monitoring electrode on the outer circumferential surface of the catheter conduit; and the third monitoring electrode which is arranged to be spaced apart from the second monitoring electrode on the outer circumferential surface of the catheter conduit; wherein the first monitoring electrode, the second monitoring electrode, the ablation electrode unit, the third monitoring electrode are arranged in succession in a direction from the end of the distal portion to the proximal portion.

In the first embodiment, it is preferable that the mapping ablation catheter further comprises: the first electric wire which is connected between the monitoring electrode unit and the current application unit in the catheter conduit and which supplies the first current to the monitoring electrode unit; and the second electric wire which is connected between the ablation electrode unit and the current application unit in the catheter conduit and which supplies the second current to the ablation electrode unit.

In the first embodiment, it is preferable that the monitoring electrode unit detects the lesion region by supplying the first current from the current application unit to the human body, and that the ablation electrode unit supplies the second current from the current application unit to the lesion region, when the ablation electrode unit is being in side-contact with the lesion region by which the monitoring electrode has passed through the movement of the catheter conduit.

In the first embodiment, it is preferable that the catheter conduit is made of insulating material to prevent current applied to the monitoring electrode unit and the ablation electrode unit from flowing.

In the first embodiment, it is preferable that the catheter conduit is configured such that the distal portion of the catheter conduit is inserted into the human body through a vessel.

In the first embodiment, it is preferable that the liquid supply unit further comprises a liquid receiving member which is connected to the other end of the liquid supply tube at the opposite of the catheter conduit; and the liquid supply unit makes liquid contained in the liquid receiving member to be discharged to the human body through the liquid supply tube and the liquid discharge hole, the liquid discharge hole is closed by the contact with the lesion region when the ablation electrode is in contact with the lesion region, and liquid is injected to the lesion region through the liquid discharge hole which is not in contact with the lesion region, thereby increasing an electric conductivity of the current applied to the ablation electrode to the lesion region.

In the second embodiment, it is preferable that the monitoring electrode unit consists of a plurality of monitoring electrodes which are arranged to be spaced apart from each other in series in a direction from the end of the distal portion to the proximal portion and which are arranged to surround the outer circumferential surface of the distal portion of the catheter conduit; the ablation electrode unit consists of a plurality of ablation electrodes which are arranged to be spaced apart from each other in series in a direction from the distal portion to the proximal portion at the location which is spaced apart from the plurality of monitoring electrodes and which are arranged to surround the outer circumferential surface of the distal portion of the catheter conduit, to remove the plurality of lesion regions when current is applied; the plurality of monitoring electrodes and the plurality of ablation electrodes are arranged in succession on the outer circumferential surface of the catheter conduit from the end of the distal portion to the proximal portion; and the plurality of ablation electrodes are in side-contact with the plurality of lesion regions when the catheter conduit is inserted into the cardiac organ.

In the second embodiment, it is preferable that the current application unit is configured to selectively apply an ablation current to the ablation electrode which is in contact with the lesion region on which the plurality of monitoring electrodes performed a mapping among the plurality of ablation electrodes, thereby removing the plurality of lesion regions which are spaced apart from each other.

In the second embodiment, it is preferable that the liquid supply unit further comprises a liquid receiving member which is connected to the other end of the liquid supply tube at the opposite of the catheter conduit, such that liquid contained in the liquid receiving member is discharged to the human body through the liquid supply tube and the liquid discharge hole; and the liquid discharge hole is closed by the contact with the lesion region when the plurality of ablation electrodes are in contact with the lesion region, and liquid is discharged to the lesion region through the discharge hole which is not in contact with the lesion region, thereby increasing the electric conductivity of the current applied to the plurality of ablation electrodes to the lesion region.

In the second embodiment, it is preferable that the current application unit comprises: a current application connector which is connected to a hand manipulation unit; a plurality of mapping wires which have one end which is connected to the plurality of monitoring electrodes in the catheter conduit and the other end which is connected to the current application connector and which supplies a mapping current to the plurality of monitoring electrodes; and a plurality of ablation wires which have one end which is connected to the plurality of ablation electrodes in the catheter conduit and the other end which is connected to the current application connector and which supplies an ablation current to the plurality of ablation electrodes.

Advantageous Effect

According to the present invention, a monitoring electrode, a liquid discharge hole and an ablation electrode are arranged in consecutive order in a direction from the end of the distal portion to the proximal portion of the catheter conduit, differently from a conventional catheter having an ablation electrode at the end of the distal portion of the catheter. Therefore, the catheter of the invention can increase the contact area between the ablation electrode and the lesion region so that an electric current can be provided to the lesion region even when the position of the catheter conduit is changed slightly due to the heart beat, whereby the operator can perform a catheter operation more stably.

Meanwhile, the conventional catheter is configured such that the ablation electrode is installed on the end of the distal portion of the catheter and the monitoring electrode for mapping the lesion region is spaced apart from the ablation electrode by a predetermined distance. During the catheter operation, after the end of the distal portion of the catheter inserted into the lesion region from the outside of the human body passes by the lesion region, the monitoring electrode unit 112 detects the lesion region and then the ablation electrode returns to the lesion region by the position adjustment of the catheter operator so as to cure the lesion region. Differently from the conventional catheter, according to the invention, a monitoring electrode, a liquid discharge hole and an ablation electrode are arranged in consecutive order in a direction from the end of the distal portion of the catheter conduit to the proximal portion of the catheter conduit. After the distal portion of the catheter conduit is inserted into the human body, the monitoring electrode performs a mapping on the lesion region, and then the distal portion of the catheter conduit is further pushed into the human body so that the ablation electrode is moved to the position where the monitoring electrode has already passed. Therefore, the above feature according to the present invention increases the convenience of a catheter operator.

Further, according to the invention, a monitoring electrode, a liquid discharge hole and an ablation electrode are arranged in consecutive order in a direction from the end of the distal portion to the proximal portion of the catheter conduit such that liquid discharged from the liquid discharge hole is discharged uniformly to the monitoring electrode and the ablation electrode. Therefore, the electric conductivity of the monitoring electrode and the ablation electrode can be increased and the mapping and the ablation of lesion regions can be carried out more efficiently.

According to the invention, lesion regions on the cardiac organ can be mapped with a minimum mapping using a plurality of mapping electrodes, and a plurality of ablation electrodes can be in contact with lesion regions on the cardiac organ, so that lesion regions which are in contact with the plurality of ablation electrodes can be removed simultaneously with one application of ablation current.

MODE FOR CARRYING OUT THE INVENTION

Figure 1:
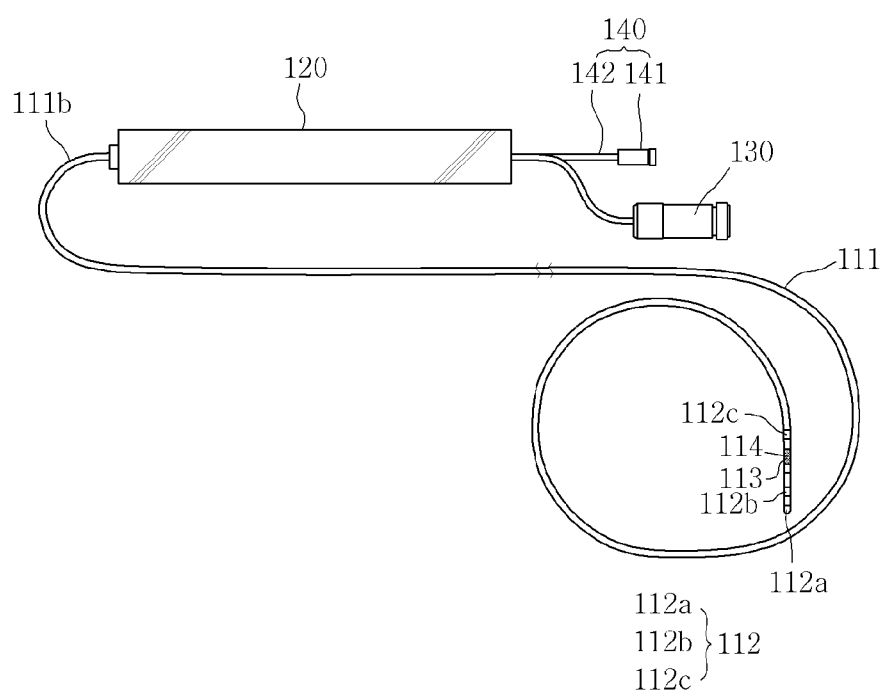
FIG. 1 is a schematic view of a mapping ablation catheter according to the first embodiment of the present invention.

Hereinafter, preferred embodiments of a mapping ablation catheter according to the present invention will be explained in detail referring to attached drawings. Regarding reference numerals, it should be understood that the same constitutional elements have the same reference numeral and the explanation thereof may be omitted when necessary.

First Embodiment

As shown in FIG. 1, the mapping ablation catheter 100 according to the present embodiment comprises a catheter conduit 111, a monitoring electrode unit 112, an ablation electrode 114, a hand manipulation unit 120, a current application unit 130 and a liquid supply unit 140. The catheter 100 according to the present embodiment can be inserted into the cardiac organ through a blood vessel and remove a lesion region (X) from the cardiac organ without need to perform laparotomy about the entire part on which a surgery is required.

For clarity's sake, based on a position of an operator during operation, a portion of the catheter conduit 111 near an operator is referred to as a proximal part and a portion of the catheter conduit 111 away from an operator is referred to as a distal part of the catheter conduit 111.

It is preferable that the catheter conduit 111 according to the present embodiment has a length by which the catheter conduit can be inserted into the body organ such as cardiac organ through vessel of a person who is under the operation (patient) from a position of a surgeon (doctor).

The catheter conduit 111 according to the present embodiment is configured to be inserted into vessel. In the present embodiment, a monitoring electrode unit 112 and an ablation electrode 114 are arranged on the outer circumferential surface of the distal portion of the catheter conduit 111. In the embodiment, preferably, the catheter conduit 111 is made of insulating material to prevent current applied to the ablation electrode 114 and the monitoring electrode unit 112 from flowing.

Preferably, the catheter conduit 111 is shaped such that the distal portion is closed and the conduit is hollow inside. A first electric wire 131, a second electric wire 132 and a guide member 115 are installed in the catheter conduit 111.

In the present embodiment, the guide member 115 has one end which is arranged on the end of the distal portion of the catheter conduit 111 inside the catheter conduit 111 and the other end which is connected to the hand manipulation unit 120. The guide member 115 can be operated such that by the manipulation of the hand manipulation unit 120, one end of the guide member 115, i.e., the end of the distal portion of the catheter conduit 111, is straightened or is rolled to be curved.

In the mapping ablation catheter 100 according to the present embodiment, when the catheter conduit 111 is inserted into the body along vessel, is inserted into the cardiac organ and then moves from the right atrium to the left atrium, the shape of the distal portion of the catheter conduit 111 can be varied by the hand manipulation unit 120 so as to reach the lesion region (X) more easily.

In the embodiment, the hand manipulation unit 120 is connected to the proximal portion of the catheter conduit 111. In this regard, one end of the hand manipulation unit 120 is connected to the catheter conduit 111 and the other end is connected to the current application unit 130 and the liquid supply unit 140.

As shown in FIG. 1, the hand manipulation unit 120 according to the embodiment is a member whose one side is connected to the guide member 115 at the proximal portion of the catheter conduit 111 to adjust the curvature of the distal portion of the catheter conduit 111. The other side of the hand manipulation unit 120 is connected to the current application unit 130 and the liquid supply unit 140.

In the embodiment, the current application unit 130 is a member which is connected to the hand manipulation unit 120 at the opposite side of the catheter conduit 111 to apply current to the monitoring electrode unit 112 and the ablation electrode 114. The current application unit 130 is provided with the first electric wire 131 and the second electric wire 132.

Figure 3:
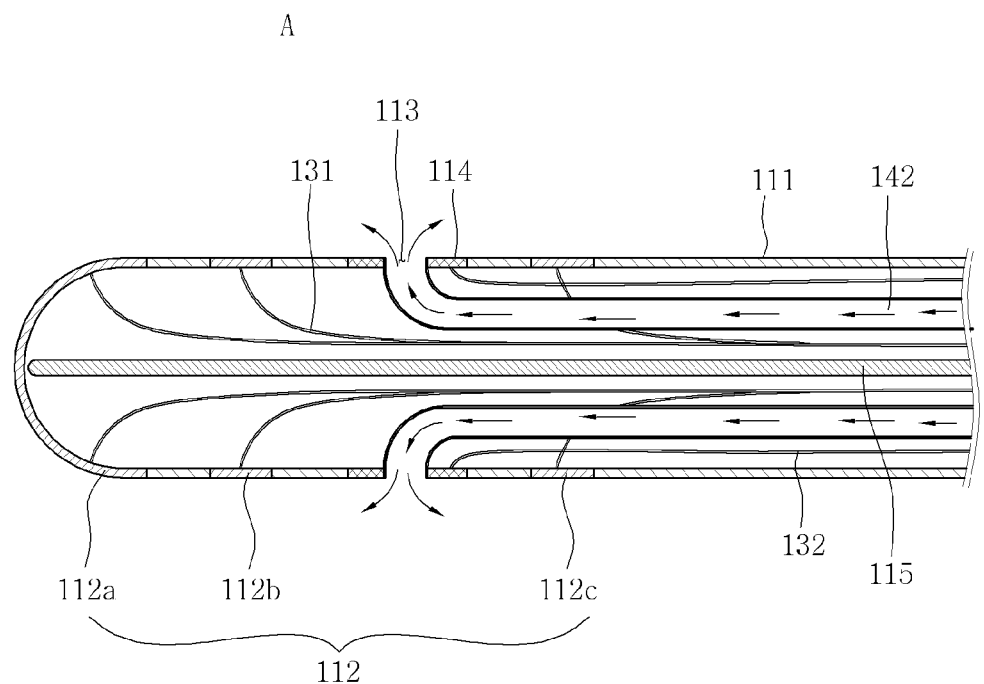
FIG. 3 is a view showing the inner cross section taken from A portion of FIG. 2.

As shown in FIG. 3, the first electric wire 131 is disposed in the catheter conduit 111 and one end of the first electric wire is connected to the monitoring electrode unit 112 so that the first current from the current application unit 130 is provided to the monitoring electrode unit 112.

The second electric wire 132 is arranged in the catheter conduit 111 separately from the first electric wire 131 and one end of the second electric wire is connected to the ablation electrode 114 so that the second current from the current application unit 130 is provided to the ablation electrode 114.

Preferably, in the embodiment, the first current has an intensity of current to a degree that the monitoring electrode unit 112 generates a low frequency and the second current has an intensity of current to a degree that the ablation electrode 114 generates a high frequency to remove the lesion region (X).

Meanwhile, the mapping ablation catheter 100 according to the embodiment has a liquid supply unit 140 which supplies liquid to the monitoring electrode unit 112 and the ablation electrode 114 so as to increase the electrical conductivity of the monitoring electrode unit 112 and the ablation electrode 114.

Here, the liquid supply unit 140 has a liquid receiving member 141 and a liquid supply tube 142. Normal saline solution which is harmless to human body and increases an electric conductivity of the monitoring electrode unit 112 and the ablation electrode 114 will be appropriate to use for liquid which is injected to human organ. However, liquid which is injected to human organ is not limited to normal saline solution. The type of liquid can be varied within the scope expected from those skilled in the art.

In the embodiment, the liquid receiving member 141 is a member to receive liquid and is connected to the hand manipulation unit 120 at the opposite side of the catheter conduit 111. The liquid receiving member 141 is connected to the liquid supply tube 142.

Here, the liquid supply tube 142 has one end which is connected to a liquid discharge hole 113 in the catheter conduit 111 and the other end which is connected to the liquid receiving member 141. Liquid which flows in the liquid supply tube 142 according to the embodiment is injected outwards through the liquid discharge hole 113.

The mapping ablation catheter 100 according to the embodiment is configured such that the ablation electrode 114 is in side-contact with the lesion region (X). Here, "side-contact" means that some portion of the outer circumferential surface of the ablation electrode 114 is in contact with the lesion region (X). In detail, the mapping ablation catheter 100 is configured such that the ablation electrode 114 is arranged to surround the outer circumferential surface of the distal portion of the catheter conduit 111 at the position which is spaced apart from the end of the catheter conduit 111. In this configuration, the ablation electrode 114 is configured such that some of the area of the ablation electrode 114 are in contact with the lesion region (X), instead of the ablation electrode being in contact with the lesion region (X) in the form of cusp. In the description, for clarity's sake, the term 'side-contact' refers to the portion where some of the outer circumferential surface of the ablation electrode 114 is in contact with the lesion region (X).

The mapping ablation catheter 100 is configured such that the liquid discharge hole 113 is closed by the contact with the lesion region (X) when the ablation electrode 114 is in contact with the lesion region (X) and such that liquid is injected to the lesion region (X) when the liquid discharge hole 113 is open where the liquid discharge hole 113 is not in contact with the lesion region (X). Therefore, the mapping ablation catheter 100 injects liquid from the liquid discharge hole 113, uniformly to the ablation electrode 114, so as to increase the electric conductivity of the ablation electrode 114, thereby facilitating of the ablation electrode 114 to ablate the lesion region (X) efficiently.

Hereinafter, the monitoring electrode unit 112 which performs a mapping on the lesion region and the ablation electrode 114 which ablates the lesion region will be explained.

Figure 2:
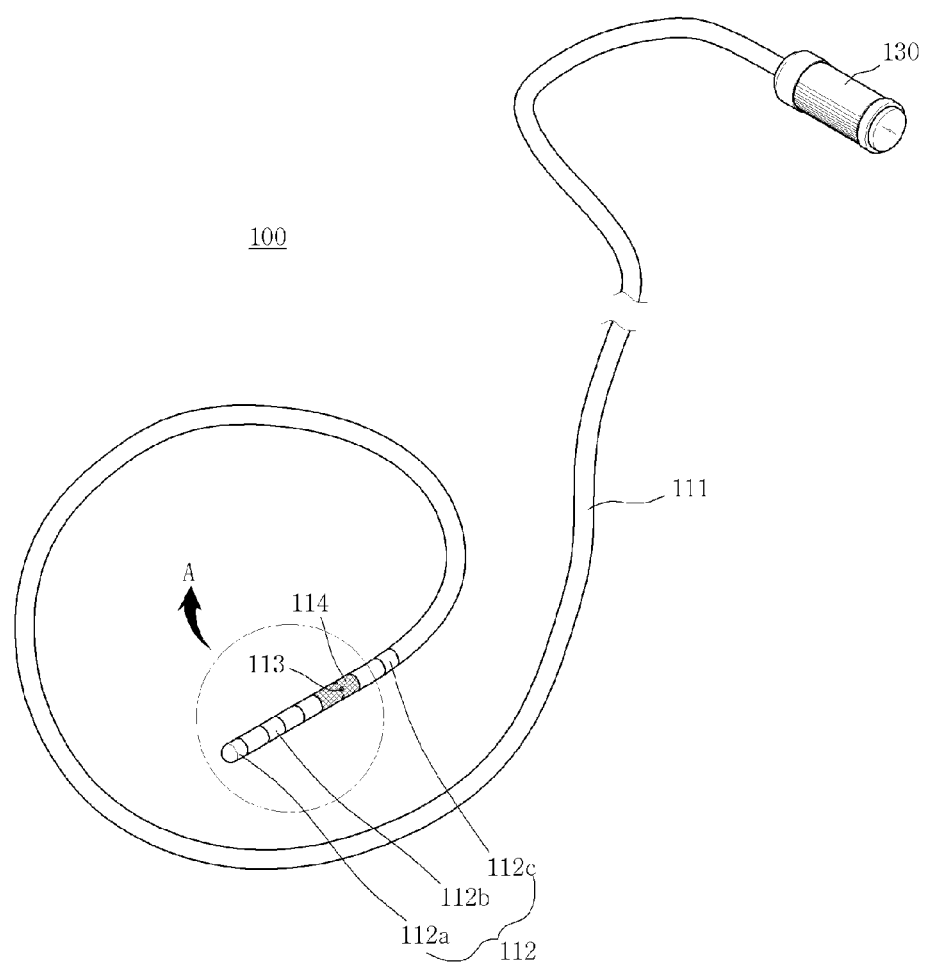
FIG. 2 is a perspective view of the mapping ablation catheter according to the first embodiment of the present invention.

In the embodiment, as shown in FIGS. 1 and 2, the monitoring electrode unit 112 is an electrode which is arranged on the outer circumferential surface of the distal portion of the catheter conduit 111. In the present embodiment, the monitoring electrode unit 112 consists of the first monitoring electrode 112a, the second monitoring electrode 112b and the third monitoring electrode 112c.

In the embodiment, the first monitoring electrode 112a is located on the end of the catheter conduit 111. The first monitoring electrode 112a is an electrode which performs a mapping on the lesion region (X) when a first current is applied.

The second monitoring electrode 112b is spaced apart from the first monitoring electrode 112a with a predetermined distance and is arranged on the outer circumferential surface of the distal portion of the catheter conduit. The second monitoring electrode is also an electrode to perform a mapping on the lesion region (X) like the first monitoring electrode 112a.

The third monitoring electrode 112c is spaced apart from the second monitoring electrode 112b by a predetermined distance and is disposed on the outer circumferential surface of the catheter conduit. The third monitoring electrode is an electrode which performs a mapping on the lesion region (X), like the first monitoring electrode 112a. The ablation electrode 114 is located between the second monitoring electrode 112b and the third monitoring electrode 112c.

As shown in FIG. 3, the first monitoring electrode 112a, the second monitoring electrode 112b and the third monitoring electrode 112c are connected to the current application unit 130 by the first electric wire 131. The lesion region (X) is harder than adjacent body tissues and thus, when current is applied to the monitoring electrode unit 112, the wavelength of current which is applied to the lesion region (X) is different from the wavelength of normal body tissue (Y).

During the operation by the catheter, an operator applies current to the monitoring electrode unit 112, and then determines the lesion region (X) by the variation of the wavelength provided to the body tissue through the monitoring electrode unit 112. The first monitoring electrode 112a, the second monitoring electrode 112b and the third monitoring electrode 112c detect the lesion region (X) while they are spaced apart from each other by a predetermined distance. Therefore, a catheter operator is able to ablate the lesion region (X) more easily by moving the ablation electrode 114 to the lesion region which is detected by one of the first monitoring electrode 112a, the second monitoring electrode 112b and the third monitoring electrode 112c.

Further, the mapping ablation catheter 100 according to the embodiment has the monitoring electrode unit 112 which is installed on the end of the distal port of the catheter conduit 111. Therefore, after the catheter conduit 111 is inserted into the body, the monitoring electrode unit 112 is firstly in contact with the body to perform a mapping on the lesion region, and then the distal portion of the catheter conduit 111 is further pushed into the body so that the ablation electrode 114 is moved to the position where the monitoring electrode unit 112 already passed.

However, in the conventional catheter, the ablation electrode 114 is installed on the end of the distal portion of the catheter and the monitoring electrode unit 112 for mapping on the lesion region (X) is spaced apart from the ablation electrode 114 by a predetermined distance. During the catheter operation, the catheter is inserted into the lesion region (X) from the outside of the human body, and after the end of the distal portion of the catheter passes the lesion region (X), the monitoring electrode unit 112 detects the lesion region (X) and then the ablation electrode 114 returns to the lesion region (X) and cure the lesion region by the position adjustment of the catheter operator.

Therefore, the above feature according to the present invention increases the convenience of a catheter operator and is different from the conventional catheter.

In the embodiment, as shown in FIGS. 1 to 3, the ablation electrode 114 is arranged on the outer circumferential surface of the distal portion of the catheter conduit 111 between the second monitoring electrode 112b and the third monitoring electrode 112c. The outer circumferential surface of the ablation electrode 114 is provided with a liquid discharge hole 113.

In the embodiment, the ablation electrode 114 is connected to the current application unit 130 by the second electric wire 132. During the catheter operation, the ablation electrode 114 according to the present invention provides a strong high-frequency to the lesion region (X) to ablate the lesion region (X).

The mapping ablation catheter 100 according to the embodiment is different from the conventional catheter in which the ablation electrode 114 provided on the end of the distal portion of the catheter is in point-contact with the lesion region (X).

Figure 4A:
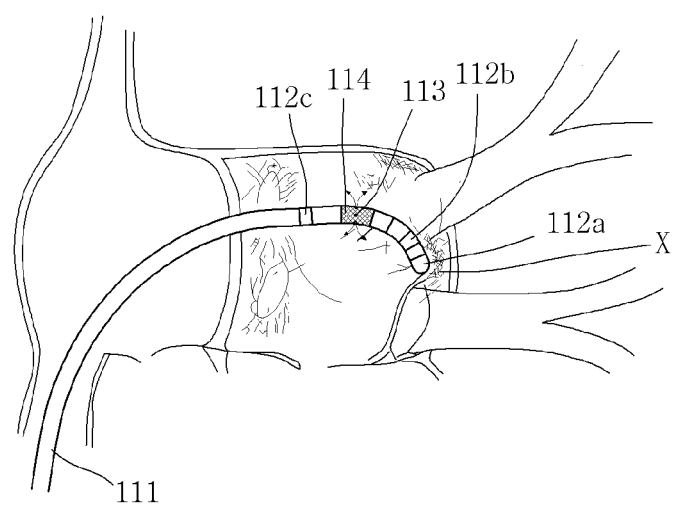
FIG. 4a shows that the mapping ablation catheter according to the first embodiment is inserted into a cardiac organ and a monitoring electrode is in contact with a lesion region.
Figure 4B:
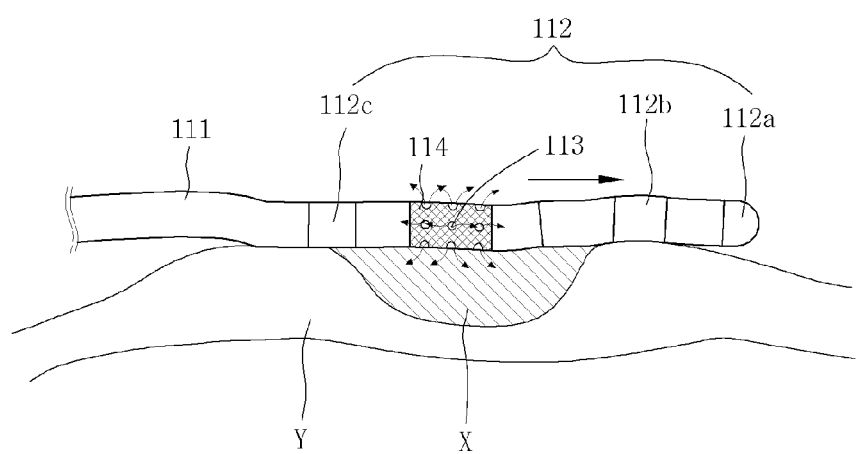
FIG. 4b shows that the mapping ablation catheter in the state of FIG. 4a is further inserted into the cardiac organ and the ablation electrode is in contact with the lesion region.

The first monitoring electrode 112a, the second monitoring electrode 112b, the ablation electrode 114 and the third monitoring electrode 112c are arranged in succession in a direction from the end of the distal portion of the catheter conduit 111 to the proximal portion of the catheter conduit. As shown in FIG. 4b, the contact area of the ablation electrode 114 can be increased by allowing the ablation electrode 114 to be in side-contact with the lesion region (X).

Therefore, even when the position of the catheter conduit 111 varies slightly due to the heart beat, it is possible to supply current to the lesion region (X) stably and thus, to allow the catheter operator to perform a catheter operation more stably.

Second Embodiment

Figure 5:
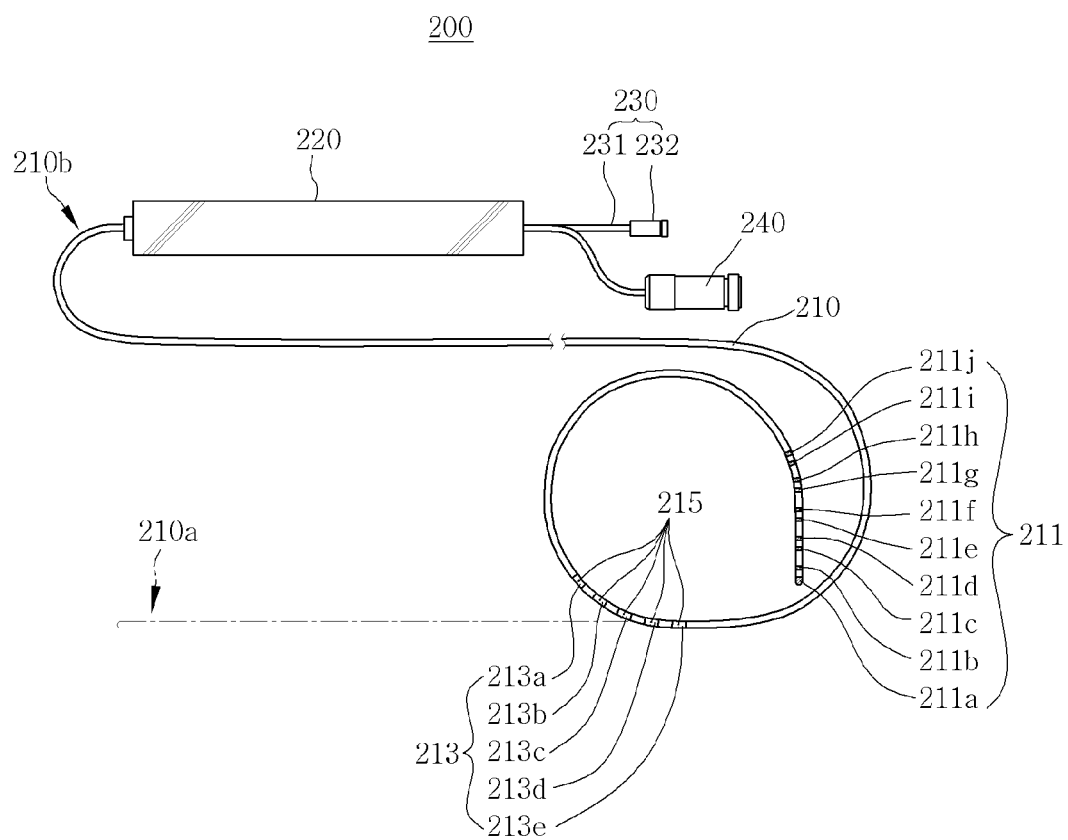
FIG. 5 is a view showing a mapping ablation catheter according to the second embodiment of the present invention.

As shown in FIG. 5, a mapping ablation catheter 200 according to the second embodiment comprises a catheter conduit 210, a plurality of monitoring electrodes 211, a plurality of ablation electrodes 213, a hand manipulation unit 220 and a liquid supply unit 230. Preferably, in the embodiment, the catheter conduit 210 is made of insulation material to prevent current applied to the plurality of ablation electrodes 213 and the plurality of monitoring electrodes 211 from flowing.

The catheter 200 according to the present embodiment is configured in such a manner that the catheter conduit 210 is inserted into the cardiac organ through a blood vessel, that a mapping is performed on the plurality of lesion regions (X) by the plurality of monitoring electrodes 211 on the distal portion 210a of the catheter conduit 210, and that the plurality of lesion regions which are in contact with the plurality of ablation electrodes 213 can be removed simultaneously by the plurality of the ablation electrodes 213.

In the embodiment, for clarity's sake, based on a position of an operator during the catheter operation, a portion of the catheter conduit 210 near an operator is referred to as a proximal part 210b of the catheter conduit 210 and a portion of the catheter conduit 210 away from an operator is referred to as a distal part 210a of the catheter conduit 210.

Preferably, the catheter conduit 210 according to the embodiment has a diameter by which the conduit can be inserted into the vessel. It is also preferable that the catheter conduit has a length by which the catheter conduit can be inserted into the body organ such as cardiac organ through vessel of a person who is under the operation (patient) from a position of a surgeon (doctor).

As shown in FIG. 5, the outer circumferential surface of the distal portion 210a of the catheter conduit 210 according to the embodiment is provided with a plurality of monitoring electrodes 211 and a plurality of ablation electrodes 213 in succession in a direction from the distal portion 210a of the catheter conduit 210 to the proximal portion 210b of the catheter conduit.

In the embodiment, the plurality of monitoring electrodes 211 are electrodes which detect lesion regions (X) on the body organ such as cardiac organ. The monitoring electrode is connected to a current application unit by a mapping wire 242. During the operation, an operator applies a mapping current to the plurality of monitoring electrodes 211 and then determines the lesion regions (X) by the variation of the wavelength which is provided to the body organ through the plurality of monitoring electrodes 211. The lesion region (X) is harder than adjacent body tissue and thus, the lesion region has different wavelength than normal body tissues when a mapping current is applied to the plurality of monitoring.

In the embodiment, for clarity's sake, the plurality of monitoring electrodes 211 are divided into and referred to as the first monitoring electrode 211a to the tenth monitoring electrode 211j, in a direction from the end of the distal portion 210a of the catheter conduit 210 to the proximal portion 210b. However, the number of the plurality of monitoring electrodes 211 is not limited to the number disclosed in the description, but can be varied within the scope expected by those skilled in the art.

Figure 6:
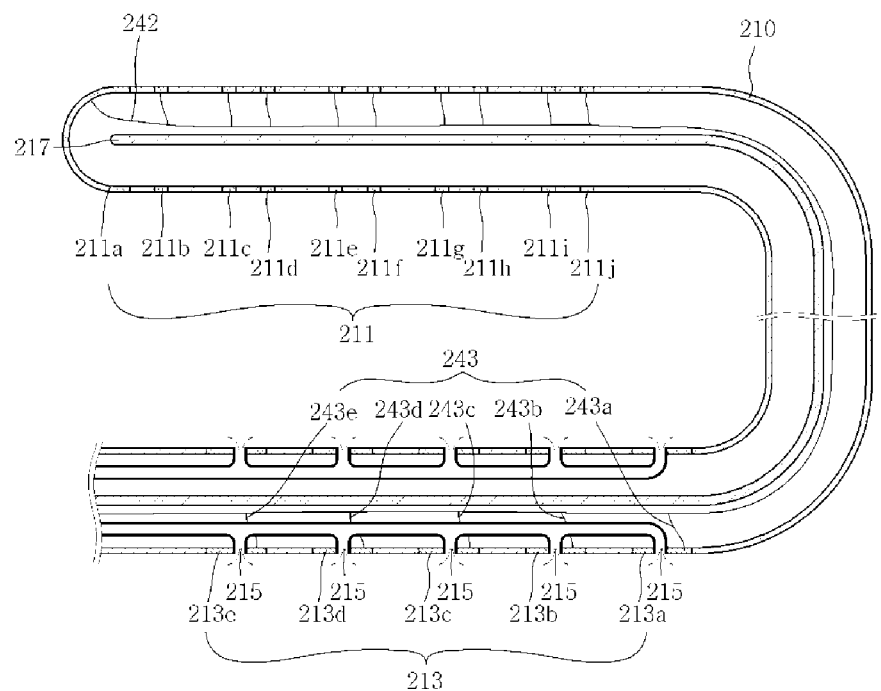
FIG. 6 is a schematic view showing the inner cross section of a distal portion of the catheter conduit corresponding to an "A" portion of FIG. 5.
Figure 7:
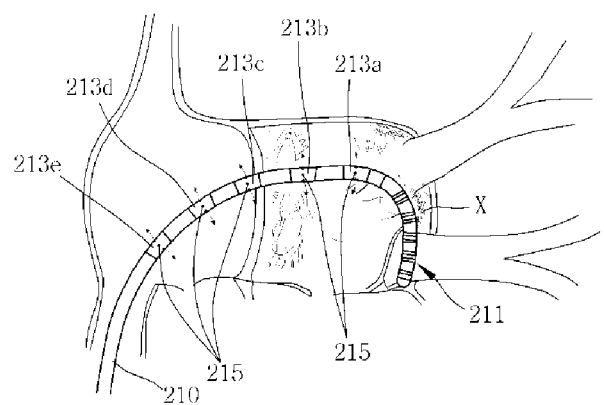
FIG. 7 shows that the mapping ablation catheter according to the second embodiment is inserted into the cardiac organ and the monitoring electrode is in contact with the lesion region.

As shown in FIGS. 5 to 7, the first monitoring electrode 211a is located on the end of the distal portion 210a of the catheter conduit 210 and the second monitoring electrode 211b is spaced apart from the first monitoring electrode 211a by a distance of about 2 mm and is located on the outer circumferential surface of the catheter conduit 210.

The third monitoring electrode 211c is spaced apart from the second monitoring electrode 211b by a distance of about 10 mm and is located on the outer circumferential surface of the distal portion 210a of the catheter conduit 210. The fourth monitoring electrode 211d is spaced apart from the third monitoring electrode 211c by a distance of about 2 mm and is located on the outer circumferential surface of the distal portion 210a of the catheter conduit 210.

The fifth monitoring electrode 211e to the tenth monitoring electrode 211j are arranged on the outer circumferential surface of the catheter conduit 210 in the same pattern as the arrangement of the first monitoring electrode 211a to the fourth monitoring electrode 211d. In the embodiment, a mapping wire 242 of the current application unit is connected to the first monitoring electrode 211a to the tenth monitoring electrode 211j, respectively.

The first monitoring electrode 211a to the tenth monitoring electrode 211j can detect the lesion region (X) on the path of the catheter conduit 210 by a mapping current applied through a mapping wire 242.

Hereinafter, the plurality of ablation electrodes 213 will be explained.

In the embodiment, the plurality of ablation electrodes 213 are spaced apart from the plurality of monitoring electrodes 211 by a predetermined distance and is installed on the outer circumferential surface of the catheter conduit 210. Here, when the ablation electrode is in contact with the lesion region (X), the ablation electrode provides a high frequency to the lesion region (X) and removes the lesion region (X).

Meanwhile, in the embodiment, for clarity's sake, the plurality of ablation electrodes 213 are divided into and referred to as the first ablation electrode 213a to the fifth ablation electrode 213e, in a direction from the end of the distal portion 210a of the catheter conduit 210 to the proximal portion 210b. However, the number of the plurality of ablation electrodes 213 is not limited to the number disclosed in the description, but can be varied within the scope expected by those skilled in the art.

As shown in FIGS. 5 to 7, the first ablation electrode 213a is spaced apart from the tenth monitoring electrode 211j by a predetermined distance and is located on the outer circumferential surface of the distal portion 210a of the catheter conduit 210.

In the embodiment, the second ablation electrode 213b is spaced apart from the first ablation electrode 213a by a distance of about 5 mm and is located on the outer circumferential surface of the distal portion 210a of the catheter conduit 210. The third ablation electrode 213c is spaced apart from the second ablation electrode 213b by a distance of about 5 mm and is located on the outer circumferential surface of the distal portion 210a of the catheter conduit 210.

The fourth ablation electrode 213d is spaced apart from the third ablation electrode 213c by a distance of about 5 mm and is located on the outer circumferential surface of the distal portion 210a of the catheter conduit 210. Lastly, the fifth ablation electrode 213e is spaced apart from the fourth ablation electrode 213d by a distance of about 5 mm and is located on the outer circumferential surface of the distal portion 210a of the catheter conduit 210.

In the embodiment, a plurality of ablation wire 243 of the current application unit are connected to the first ablation electrode 213a to the fifth ablation electrode 213e. However, in the embodiment, for clarity's sake, an ablation wire connected to the first ablation electrode 213a is referred to as the first ablation wire 243a, an ablation wire connected to the second ablation electrode 213b is referred to as the second ablation wire 243b, an ablation wire connected to the third ablation electrode 213c is referred to as the third ablation wire 243c, an ablation wire connected to the fourth ablation electrode 213d is referred to as the fourth ablation wire 243d, and an ablation wire connected to the fifth ablation electrode 213e is referred to as the fifth ablation wire 243e. The number of ablation wires connected to the plurality of the ablation electrodes 213 depends on the number of the ablation electrodes.

All or at least one of the first ablation electrode 213a to the fifth ablation electrode 213e according to the embodiment are in side-contact with the lesion region (X) and are able to remove the lesion region (X) by ablation current applied to all or at least one of the first ablation wire 243a to the fifth ablation wire 243e with the selective manipulation of the catheter operator.

In the embodiment, the first ablation electrode 213a to the fifth ablation electrode 213e are provided with a plurality of liquid discharge holes 215. In the embodiment, the liquid discharge holes 215 are arranged on the outer circumferential surface of the first ablation electrode 213a to the fifth ablation electrode 213e along the circumference of the catheter conduit 210. Therefore, the liquid discharge holes are closed by the contact with the lesion region (X) when they are in contact with the lesion region (X) of the plurality of monitoring electrodes 211 or the plurality of ablation electrodes 213. The liquid discharge holes are open to eject liquid to the lesion region (X) when the holes are not in contact with the lesion region (X).

A liquid supply tube 213 is connected to the liquid discharge holes 215 according to the embodiment. In the embodiment, the liquid supply tube 231 is an element of the liquid supply unit 230 and the liquid supply unit 230 has a liquid receiving member 232 as well as the liquid supply tube 231.

In the embodiment, the liquid supply tube 231 is configured such that one end of the liquid supply tube is connected to the liquid discharge hole 214 inside the catheter conduit 210 and the other end is connected to the liquid receiving member 232. Liquid flowing through the liquid supply tube 213 according to the embodiment is ejected to the outside from the catheter conduit 210 through the liquid discharge hole 215. In the embodiment, the liquid receiving member 232 is a member which contains liquid and is connected to the hand manipulation unit 220 at the opposite of the catheter conduit 210. The liquid supply tube 231 is connected to the liquid receiving member 232.

The mapping ablation catheter 200 according to the embodiment is configured such that liquid ejected to the outside from the catheter conduit 210 through the liquid discharge hole 215 increases the electric conductivity of ablation current, thereby allowing the first ablation electrode 213a to the fifth ablation electrode 213e to remove the lesion region (X) more easily.

That is, the mapping ablation catheter 200 allows liquid discharged from the liquid discharge hole 215 to be ejected uniformly to the first ablation electrode 213a to the fifth ablation electrode 213e, so as to increase the electric conductivity of the plurality of ablation electrodes 213. Further, the plurality of ablation electrodes 213 are in side-contact with the lesion region (X) so that the first ablation electrode 213a to the fifth ablation electrode 213e to remove the lesion region (X) more efficiently.

In the embodiment, normal saline solution which is harmless to human body and increases an electric conductivity of the ablation electrode will be appropriate to use for liquid which is injected to human organ. However, liquid which is injected to human organ is not limited to normal saline solution. The type of liquid can be varied within the scope expected from those skilled in the art.

The catheter conduit 210 according to the embodiment is hollow inside. The hollow inside of the catheter conduit 210 is provided with a guide member 217 connected to a hand manipulation unit 220, which will be described below.

In the embodiment, the guide member 217 is configured such that one end of the guide member 217 inside the catheter conduit 210 is located on the end of the distal portion 210a of the catheter conduit 210 and the other end of the guide member 217 is connected to the hand manipulation unit 220. The guide member 217 can be operated such that by the manipulation of the hand manipulation unit 220, one end of the guide member 217, i.e., the end of the distal portion 210a of the catheter conduit 210, is straightened or is rolled to be curved.

In the ablation catheter 220 according to the present embodiment, when the catheter conduit 210 is inserted into the body along vessel, is inserted into the cardiac organ and then moves from the right atrium to the left atrium, the curvature of the distal portion 210a of the catheter conduit 210 is adjusted so that the distal portion 210a of the catheter conduit 210 reaches the lesion region (X) more easily.

In the embodiment, based on the position of the hand manipulation unit 220, one end of the hand manipulation unit 220 is connected to the catheter conduit 210 and the other end is connected to the current application unit and the liquid supply unit 230, as shown in FIG. 5.

Meanwhile, the current application unit according to the embodiment comprises a current application connector 240, a plurality of mapping wire 242 and a plurality of ablation wire 243 (e.g., the first ablation wire 243a to the fifth ablation wire 243e). In the embodiment, the current application connector 240 is connected to the hand manipulation unit 220 at the opposite of the catheter conduit 210 so that the current application connector applies a mapping current to the mapping wire 242 and applies an ablation current to the first ablation wire 243a to the fifth ablation wire 243e.

In the embodiment, each of the plurality of mapping wires 242 is connected to the first monitoring electrode 211a to the tenth monitoring electrode 211j inside the catheter conduit 210. Here, the plurality of mapping wires 242 are arranged such that the mapping wires are connected to one end of the plurality of monitoring electrodes 211 inside the catheter conduit 210 as shown in FIG. 7 and the other end of mapping wires 242 is connected to the current application connector 240. Therefore, a mapping current provided by the current application connector 240 is supplied to the plurality of monitoring electrodes 211.

In the embodiment, the first ablation wire 243a to the fifth ablation wire 243e are arranged inside the catheter conduit 210, separately from the mapping wires 242 and are configured such that one end of the ablation wires is connected to the first ablation wire 213a to the fifth ablation wire 213e and the other end is connected to the current application connector 240. The first ablation wire 243a to the fifth ablation wire 243e supply ablation current from the current application connector, to all or at least one of the first ablation electrode 213a to the fifth ablation electrode 213e.

In the embodiment, the ablation current which is supplied to the first ablation electrode 213a to the fifth ablation electrode 213e through the first ablation wire 243a to the fifth ablation wire 243e is selectively provided to all or at least one of the first ablation electrode 213a to the fifth ablation electrode 213e, thereby removing lesion region (X).

That is, the current application unit can allow the ablation current to be applied to some ablation electrodes selected by the catheter operator among the plurality of ablation electrodes 213. Therefore, during the catheter operation, the catheter operator does not need to reach each of lesion regions (X) distributed on several spots of the body organ, and the plurality of ablation electrodes 213 spaced apart from each other by a predetermined distance can be simultaneously in contact with several lesion regions (X) to remove the lesion regions (X) when the ablation current is applied.

Preferably, in the embodiment, the mapping current has an intensity of current to a degree that the monitoring electrode generates a low-frequency, but the ablation current has an intensity of current to a degree that the ablation electrode generates a high-frequency to remove the lesion region (X).

The mapping ablation catheter 200 according to the embodiment has a plurality of monitoring electrodes 211 which are installed on the end of the distal port 210a of the catheter conduit 210. Therefore, after the catheter conduit 210 is inserted into the body, the plurality of monitoring electrodes 211 is firstly in contact with the body organ to perform a mapping on a plurality of lesion regions, and then the distal portion 210a of the catheter conduit 210 is further pushed into the body so that the plurality of ablation electrode 213 are moved to the positions where the plurality of monitoring electrodes 211 already passed.

However, in the conventional catheter, the ablation electrode is installed on the end of the distal portion 210a of the catheter and the monitoring electrode for mapping on the lesion region (X) is spaced apart from the ablation electrode by a predetermined distance. During the catheter operation, the catheter is inserted into the lesion region (X) from the outside of the human body, and after the end of the distal portion 210a of the catheter passes the lesion region (X), the monitoring electrode detects the lesion region (X) and then the ablation electrode returns to the lesion region (X) and cure the lesion region by the position adjustment of the catheter operator.

Therefore, the above feature according to the present invention increases the convenience of a catheter operator and is different from the conventional catheter.

Figure 8:
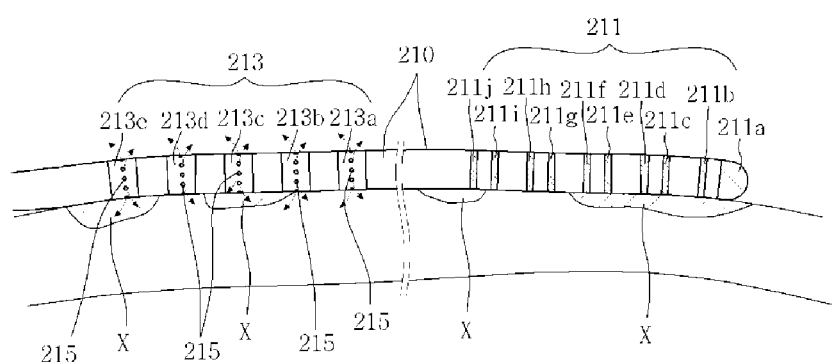
FIG. 8 shows that the mapping ablation catheter according to the second embodiment in the state of FIG. 7 is further inserted into the cardiac organ and some of the plurality of ablation electrodes are in contact with a plurality of lesion regions.

The mapping ablation catheter 200 according to the embodiment is different from the conventional catheter in which the ablation electrode provided on the end of the distal portion 210a of the catheter is in point-contact with the lesion region (X). The plurality of monitoring electrode 211 and the plurality of ablation electrodes 213 are arranged in succession in a direction from the end of the distal portion 210a of the catheter conduit 210 to the proximal portion 210b of the catheter conduit. As shown in FIG. 8, the contact area of the ablation electrode can be increased by allowing the ablation electrode to be in side-contact with the lesion region (X). Therefore, even when the position of the catheter conduit 210 varies slightly due to the heart beat, it is possible to supply current to the lesion region (X) stably and thus, to allow the catheter operator to perform a catheter operation more stably.

It will be appreciated that the present invention is described by the preferable embodiments, but the scope of the present invention is not limited to the embodiments. It is obvious that various modifications or variations can be made within the scope of the accompanying claims by those skilled in the art although they are not provided in the embodiment and all the modifications or variations are within the scope of the invention.

The invention claimed is:

1. A mapping ablation catheter having a distal portion for insertion into a human body to cure a lesion region, comprising:
   a catheter conduit comprising a hollow inner space in which a guide member is disposed;
   a monitoring electrode unit comprising a plurality of monitoring electrodes, and configured to map the lesion region by being in side-contact with a cardiac organ when the catheter conduit is inserted into the cardiac organ;
   an ablation electrode unit comprising a plurality of ablation electrodes, and configured to remove the lesion region when current is applied;
   a plurality of liquid discharge holes arranged on an outer circumferential surface of an ablation electrode among the plurality of ablation electrodes;
   a current application unit configured to apply current to the monitoring electrode unit and the ablation electrode unit; and
   a liquid supply unit comprising a liquid supply tube,
   wherein an end of the liquid supply tube is connected to the plurality of liquid discharge holes,
   wherein the plurality of monitoring electrodes are spaced apart from each other in series in a direction from an end of a distal portion of the catheter conduit to a proximal portion of the catheter conduit, and surround an outer circumferential surface of the distal portion of the catheter conduit,
   wherein the plurality of ablation electrodes are spaced apart from each other in series in a direction from the distal portion of the catheter conduit to the proximal portion of the catheter conduit at a location spaced apart from the plurality of monitoring electrodes, and surrounds the outer circumferential surface of the distal portion of the catheter conduit,
   wherein the plurality of ablation electrodes are spaced apart from each other at regular intervals,
   wherein a first monitoring electrode, among the plurality of monitoring electrodes, is located on the end of the distal portion of the catheter conduit,
   wherein a second monitoring electrode, among the plurality of monitoring electrodes, is spaced apart from the first monitoring electrode by a narrow gap, and is located on the outer circumferential surface of the distal portion of the catheter conduit,
   wherein a third monitoring electrode, among the plurality of monitoring electrodes, is spaced apart from the second monitoring electrode by an interval of five times the narrow gap, and is located on the outer circumferential surface of the distal portion of the catheter conduit,
   wherein a fourth monitoring electrode, among the plurality of monitoring electrodes, is spaced apart from the third monitoring electrode by a distance of about 2 mm, and is located on the outer circumferential surface of the distal portion of the catheter conduit, and
   wherein fifth to tenth monitoring electrodes, among the plurality of monitoring electrodes, are arranged on the outer circumferential surface of the catheter conduit in a same pattern as an arrangement of the first to fourth monitoring electrodes.

2. The mapping ablation catheter according to claim 1, wherein the current application unit is further configured to selectively apply an ablation current to the plurality of ablation electrodes to remove a plurality of lesion regions that are spaced apart from each other.

3. The mapping ablation catheter according to claim 1, wherein
   the liquid supply unit further comprises a liquid receiving member connected to another end of the liquid supply tube, and configured such that liquid contained in the liquid receiving member is discharged to the human body through the liquid supply tube and the plurality of liquid discharge holes, and
   some of the plurality of liquid discharge holes are configured to be closed by contact with the lesion region when the plurality of ablation electrodes are in contact with the lesion region, so that liquid is discharged to the lesion region through others of the plurality of liquid discharge holes which are not in contact with the lesion region, thereby increasing an electric conductivity of a current path from the plurality of ablation electrodes to the lesion region.

4. The mapping ablation catheter according to claim 1, wherein the current application unit comprises
   a current application connector connected to a hand manipulation unit,
   a plurality of mapping wires having an end connected to the plurality of monitoring electrodes in the catheter conduit and another end connected to the current application connector, and configured to supply a mapping current to the plurality of monitoring electrodes, and
   a plurality of ablation wires having an end connected to the plurality of ablation electrodes in the catheter conduit and another end connected to the current application connector, and configured to supply an ablation current to the plurality of ablation electrodes.

* * * * *